(12) United States Patent
Li et al.

(10) Patent No.: US 9,220,303 B2
(45) Date of Patent: Dec. 29, 2015

(54) CARTRIDGE, ATOMIZING DEVICE AND ELECTRONIC CIGARETTE HAVING SAME

(71) Applicant: Shenzhen First Union Technology Co., Ltd., Shenzhen (CN)

(72) Inventors: Yonghai Li, Shenzhen (CN); Zhongli Xu, Shenzhen (CN); Zhanpanbo Xia, Shenzhen (CN); Yunping Zhong, Shenzhen (CN)

(73) Assignee: Shenzhen First Union Technology Co., Ltd., Shenzhen (CN)

( * ) Notice: Subject to any disclaimer, the term of this patent is extended or adjusted under 35 U.S.C. 154(b) by 0 days.

(21) Appl. No.: 14/189,636

(22) Filed: Feb. 25, 2014

(65) Prior Publication Data

US 2014/0332020 A1 Nov. 13, 2014

(30) Foreign Application Priority Data

May 8, 2013 (CN) .................. 2013 2 0242989 U
May 29, 2013 (CN) .................. 2013 1 0204714

(51) Int. Cl.
  *A24F 47/00* (2006.01)
  *F22B 1/28* (2006.01)
  *A61M 15/06* (2006.01)
  *A61M 11/04* (2006.01)

(52) U.S. Cl.
  CPC .............. *A24F 47/008* (2013.01); *A24F 47/002* (2013.01); *A61M 11/042* (2014.02); *A61M 15/06* (2013.01); *F22B 1/284* (2013.01); *A61M 2205/3653* (2013.01); *A61M 2205/8206* (2013.01)

(58) Field of Classification Search
  CPC ..... A24F 47/002; A24F 47/008; A61M 15/06
  USPC ................... 131/273, 329; 128/202.21
  See application file for complete search history.

(56) References Cited

U.S. PATENT DOCUMENTS

| | | | |
|---|---|---|---|
| 8,353,426 B2 * | 1/2013 | Wold et al. | 222/1 |
| 2010/0031968 A1 * | 2/2010 | Sheikh et al. | 131/347 |
| 2013/0160764 A1 * | 6/2013 | Liu | 128/202.21 |

FOREIGN PATENT DOCUMENTS

| | | |
|---|---|---|
| CN | 1040496 | 3/1990 |
| CN | 201709398 | 1/2011 |
| CN | 201767029 | 3/2011 |
| CN | 201781984 | 4/2011 |
| CN | 201830900 | 5/2011 |
| CN | 201888252 | 7/2011 |
| CN | 202005248 | 10/2011 |
| CN | 202197836 | 4/2012 |
| CN | 202407083 | 9/2012 |
| CN | 202603607 | 12/2012 |
| CN | 202635602 | 1/2013 |
| CN | 102920028 | 2/2013 |
| CN | 202890464 U | 4/2013 |
| JP | 2008104966 | 5/2008 |
| WO | WO-0132247 A1 | 5/2001 |
| WO | WO-2011146174 A3 | 2/2012 |

* cited by examiner

*Primary Examiner* — Anthony Calandra
(74) *Attorney, Agent, or Firm* — Winstead PC

(57) ABSTRACT

A cartridge of an electronic cigarette includes an oil reserving pipe, an oil obstructing plug and a heating assembly. The oil reserving pipe has an inner space for reserving a tobacco oil. The oil obstructing plug is arranged at an end of the oil reserving pipe and has an oil hole in communication with the inner space. The heating assembly is arranged under the oil obstructing plug and configured for heating and atomizing the tobacco oil penetrating through the oil hole. An atomizing device using the cartridge, and an electronic device using the atomizing device are also provided.

16 Claims, 10 Drawing Sheets

CARTRIDGE, ATOMIZING DEVICE AND ELECTRONIC CIGARETTE HAVING SAME

BACKGROUND

1. Technical Field

The present invention relates to electronic cigarettes, and particularly to a cartridge, an atomizing device and an electronic cigarette having the cartridge and the atomizing device.

2. Description of Related Art

Atomizing devices are key components of electronic cigarettes. A typical atomizing device includes a cartridge having an oil reserving pipe and a heating assembly arranged on the oil reserving pipe and configured for heating and atomizing an tobacco oil. However, by this configuration, when the amount of the tobacco oil is less than a certain level, the heating assembly cannot contact the remaining tobacco oil, therefore the remaining tobacco oil cannot be heated and atomized.

What is needed, therefore, is a cartridge, an atomizing device and an electronic cigarette which can overcome the above shortcomings.

BRIEF DESCRIPTION OF THE DRAWINGS

Many aspects of the present cartridge, atomizing device and electronic cigarette can be better understood with reference to the following drawings. The components in the drawings are not necessarily drawn to scale, the emphasis instead being placed upon clearly illustrating the principles of the present cartridge, atomizing device and electronic cigarette. Moreover, in the drawings, like reference numerals designate corresponding parts throughout the several views.

DETAILED DESCRIPTION

Embodiments of the present atomizing device and electronic cigarette will now be described in detail below and with references to the drawings.

Figure 1:
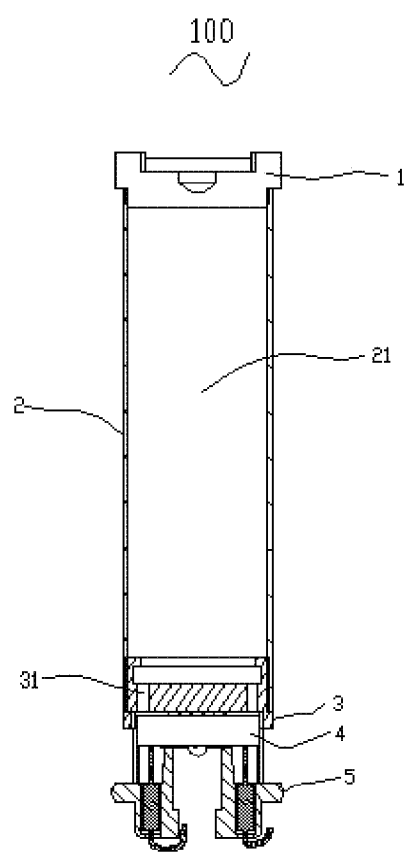
FIG. 1 is a schematic cross sectional view of a cartridge of an electronic cigarette in accordance with a first embodiment.

Referring to FIG. 1, a cartridge 100 of an electric cigarette in accordance with a first embodiment is provided. The cartridge 100 mainly includes an oil reserving pipe 2, a sealing cover 1, an oil obstructing plug 3, a heating assembly 4 and a heating assembly fixing base 5. The sealing cover 1 and the oil obstructing plug 3 are arranged at two ends of the oil reserving pipe 2. The heating assembly 4 and the heating assembly fixing base 5 are arranged under the oil obstructing plug 3.

Figure 2:
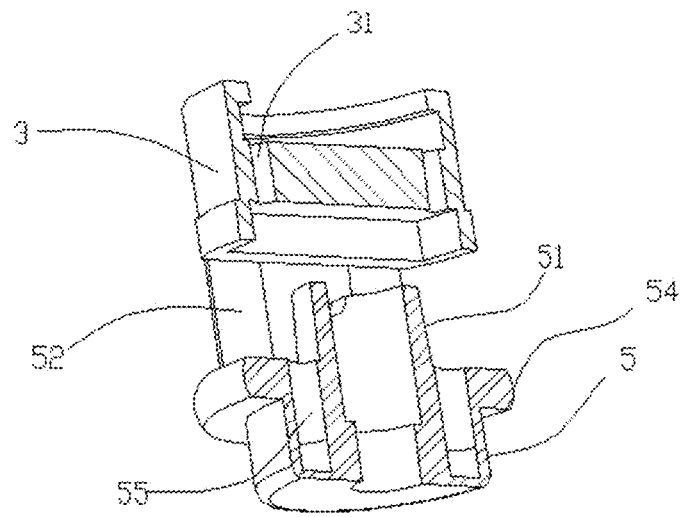
FIG. 2 is a schematic isometric cut-away view of an oil obstructing plug and a heating assembly fixing base shown in FIG. 1.
Figure 5:
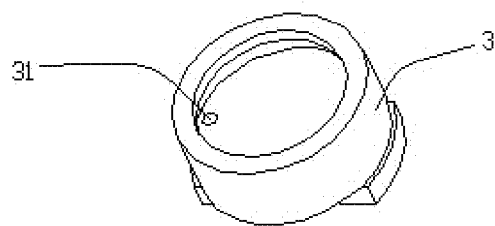
FIG. 5 is a schematic isometric view of the oil obstructing plug shown in FIG. 2.

The oil reserving pipe 2 has an inner space 21 for reserving tobacco oil, and the inner space 21 does not have an oil reserving cotton for reserving the tobacco oil. Referring to FIG. 2 and FIG. 5, the oil obstructing plug 3 has two oil holes 31 formed therethrough. A cross sectional area of each of the oil holes 31 is in a range between 0.5-2.2 $mm^2$ In other embodiments, the oil holes 31 can be replaced by cutouts formed in an outer wall of the oil obstructing plug 3.

Figure 4:
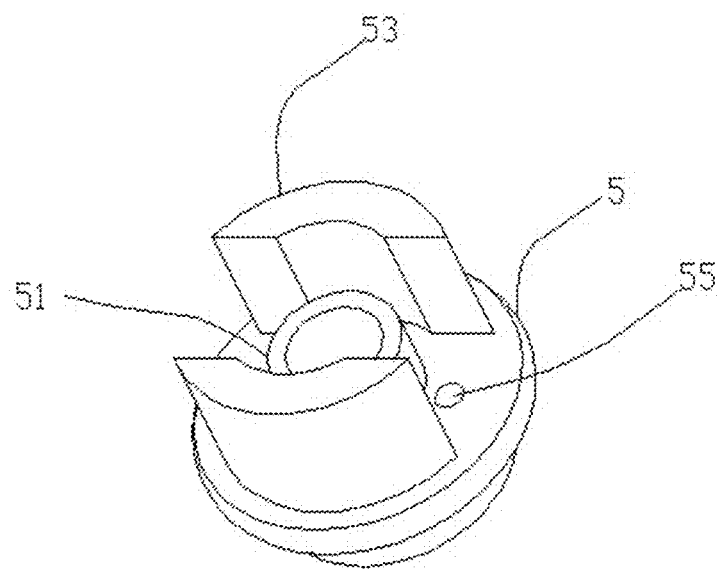
FIG. 4 shows a heating assembly positioned on the heating assembly fixing base of FIG. 3.

Referring to FIG. 2 and FIG. 4, the heating assembly fixing base 5 includes an annular projection 51, a flange 54 and two arms 53. The annular projection 51 extends upwards from a bottom surface of the heating assembly fixing base 5. The flange 54 extends outwards from an outer wall of the annular projection 51, and has two through holes 55 formed therethrough. The two arms 53 extend upwards from a top surface of the flange 54. A receiving space 52 is formed between the two arms 53, and the annular projection 51 is located in the receiving space 52.

Figure 3:
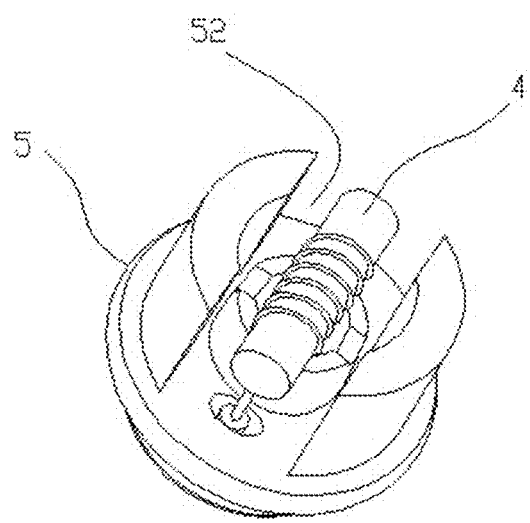
FIG. 3 is a schematic isometric view of the heating assembly fixing base shown in FIG. 2.

Referring to FIG. 3, the heating assembly 4 includes a glass fiber core 41 and a heating coil 42 surrounding the glass fiber core 41. The heating assembly 4 is positioned on the annular projection 51, and two ends of the heating coil 42 extend through the respective through holes 55 and abut on an inner wall of the annular projection 51 and an outer wall of the heating assembly fixing base 5, respectively.

Figure 6:
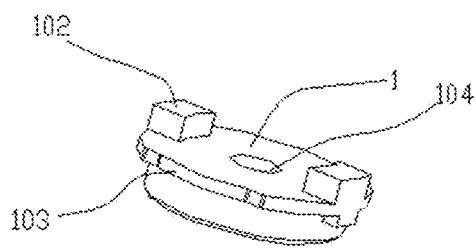
FIG. 6 is a schematic isometric view of a sealing cover shown FIG. 1.
Figure 14:
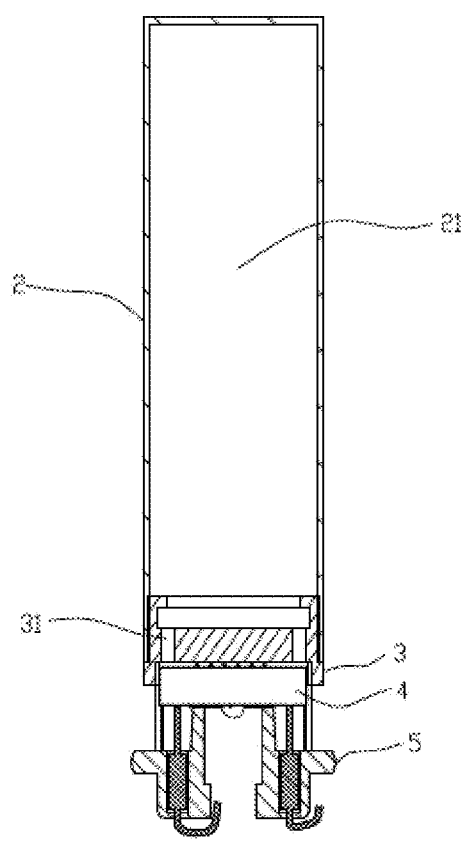
FIG. 14 is a schematic view of another configuration of an oil reserving pipe used in the cartridge.

Referring to FIG. 6, the sealing cover 1 includes two protrusions 102, an oil filling hole 104, and an air cutout 103 formed at a peripheral wall of the sealing cover 1. The sealing cover 1 can be made of a silicon dioxide, the oil filling hole 104 is a blind hole, and the oil can be filled into the inner space 21 using an injector positioned in the oil filling hole 104. In other embodiments, the oil reserving pipe 2 can be sealed at one end by a bottom wall of the oil reserving pipe 2 (see FIG. 14), and the bottom wall is integrally formed with a peripheral wall of the oil reserving pipe 2. In this situation, the sealing cover 1 can be omitted, and the oil is filled into the inner space 21 from the other end.

Figure 7:
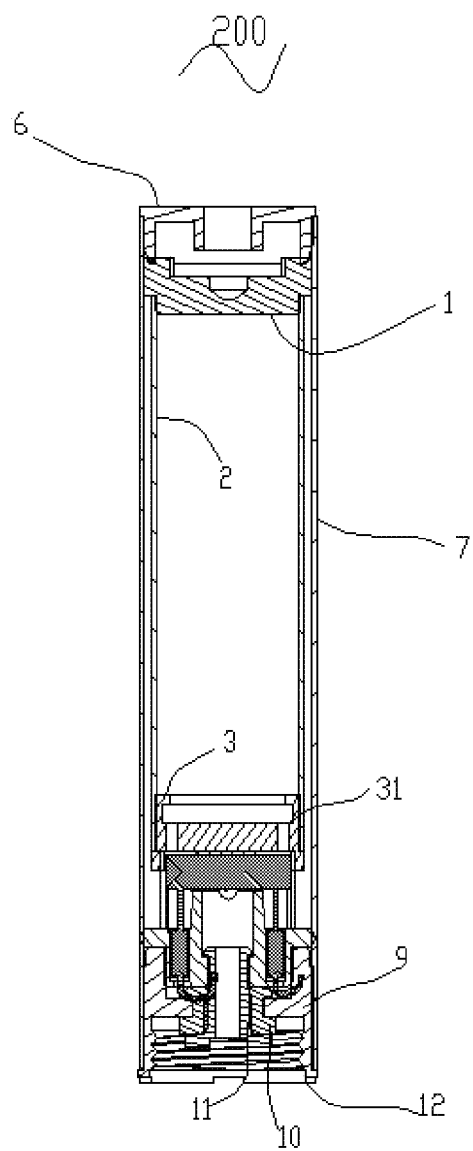
FIG. 7 is a schematic cross sectional view of an atomizing device of an electronic cigarette in accordance with a second embodiment.

Referring also to FIG. 7, in an atomizing device 200 in accordance with a second embodiment, a suction nozzle 6 and an atomizing sleeve 7 are added to the cartridge 100; in addition, an electrode assembly 12 including a screw sleeve 9, an insulated ring 10 and an electrode ring 11 is provided. The atomizing sleeve 7 receives all of the elements therein, the suction nozzle 6 is positioned at an end of the atomizing sleeve 7 and abuts on the protrusions 102 of the sealing cover 1, then the entire atomizing device can be compact. The insulated ring 10 is located between the screw sleeve 9 and the electrode ring 11, and two ends of the heating coil 42 are electrically connected to the screw sleeve 9 and the electrode ring 11. An air passage 71 is defined between the atomizing sleeve 7 and the oil reserving pipe 2, and the air cutout 103 is in communication with the air passage 71. The electrode assembly is positioned at another end of the atomizing sleeve 7, the screw sleeve 9 is configured for being threadedly connected to a battery assembly (see FIG. 13), and the screw sleeve 9 and the electrode ring 11 are respectively configured as a positive end and a negative end.

Preferably, an oil reserving cotton (not shown) can be arranged between the oil obstructing plug 3 and the heating assembly 4. In particular, the oil reserving cotton can be arranged under the oil holes 31, and in contact with the oil obstructing plug 3 and the heating assembly 4.

Figure 8:
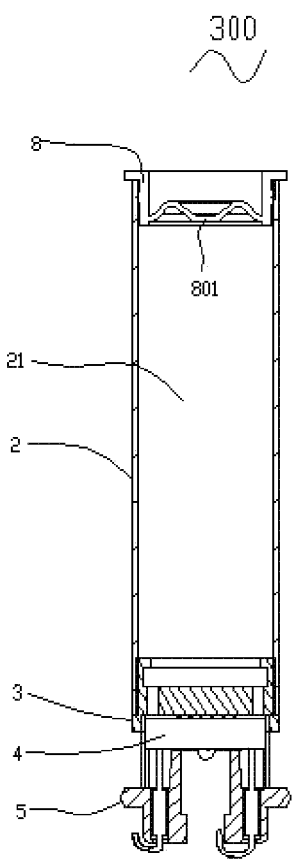
FIG. 8 a schematic cross sectional view of a cartridge of an electronic cigarette in accordance with a third embodiment.
Figure 9:
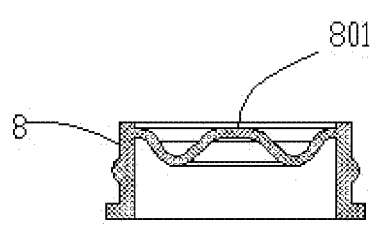
FIG. 9 is a schematic view of a sealing cover shown in FIG. 8.

Referring to FIG. 8 to FIG. 9, a cartridge 300 of an electric cigarette in accordance with a third embodiment is provided. The cartridge 300 is essentially similar to the cartridge 100 of the first embodiment, however, a sealing cover 8 having a curved air pressure adjusting portion 801 is applied on the end of the oil reserving pipe 2. The air pressure adjusting portion 801 can adjust an air pressure around the oil reserving pipe 2.

Figure 10:
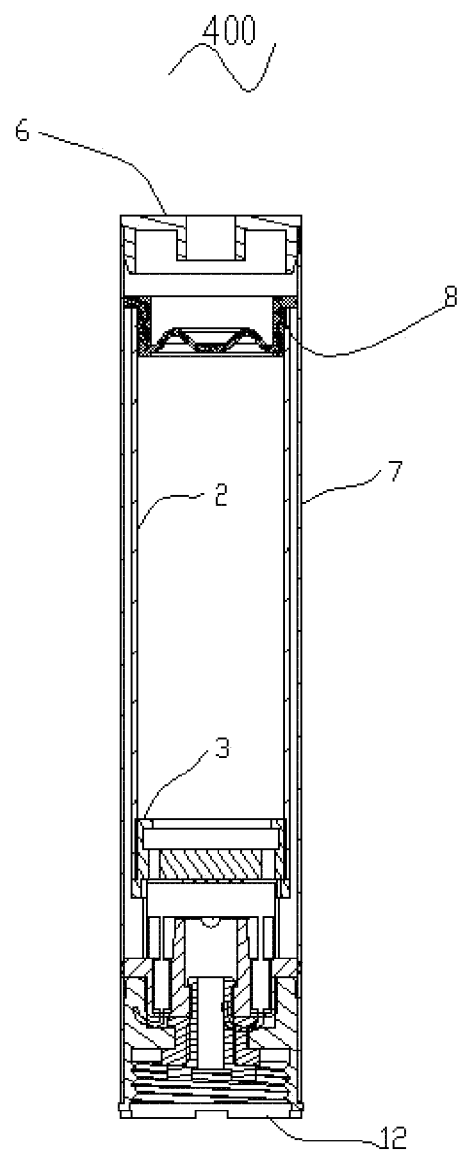
FIG. 10 is a schematic cross sectional view of an atomizing device of an electronic cigarette in accordance with a fourth embodiment.

Referring to FIG. 10, in an atomizing device 400 in accordance with a fourth embodiment, a suction nozzle 6, an atomizing sleeve 7 and an electrode assembly 12 are also added to the cartridge 200. It is understood that in order to facilitate air flow through the entire atomizing device, an air cutout (not shown) is also formed at a peripheral wall of the sealing cover 8.

Figure 11:
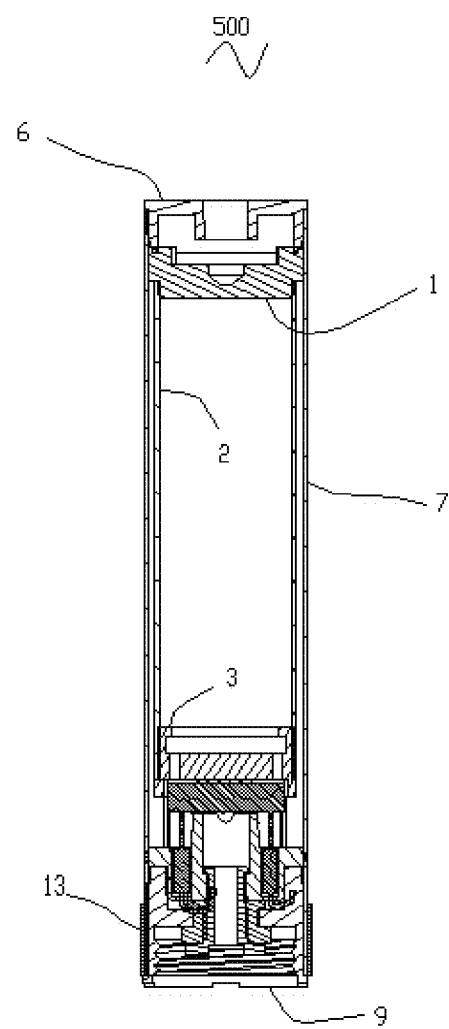
FIG. 11 is a cross sectional view of an atomizing device of an electronic cigarette in accordance with a fifth embodiment.
Figure 12:
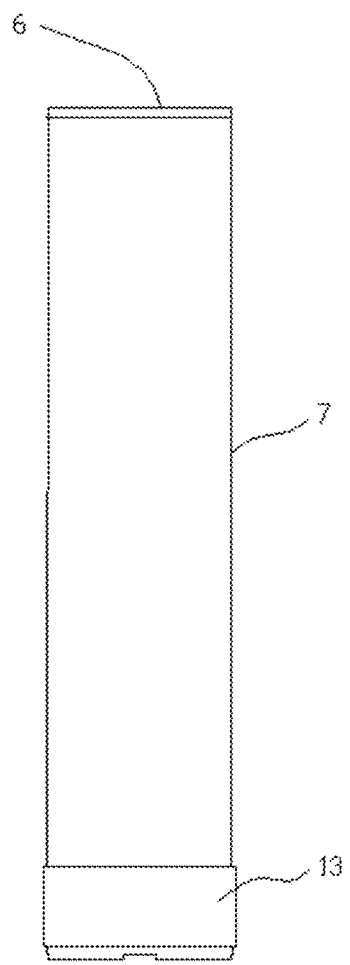
FIG. 12 shows a profile of the atomizing device of FIG. 11.

Referring to FIGS. 11 and 12, an atomizing device 500 in accordance with a fifth embodiment is provided. Relative to the atomizing device of the second embodiment, a ring-shaped fastening member 13 is added to an outer wall of the atomizing sleeve 7 at an end of the atomizing sleeve 7. The fastening member 13 is configured for fastening the atomizing sleeve 7 to the screw sleeve 9. Due to the fastening member 13, the screw sleeve 9 would not fall off from the atomizing sleeve 7. Specially, when the atomizing sleeve 7 is made of a plastic material, the fastening member 13 can be made of a metallic material, then the fastening member 13 can act as a decoration for the atomizing sleeve 7, and the fastening member 13 can avoid plastic deformation of the atomizing sleeve 7.

Figure 13:
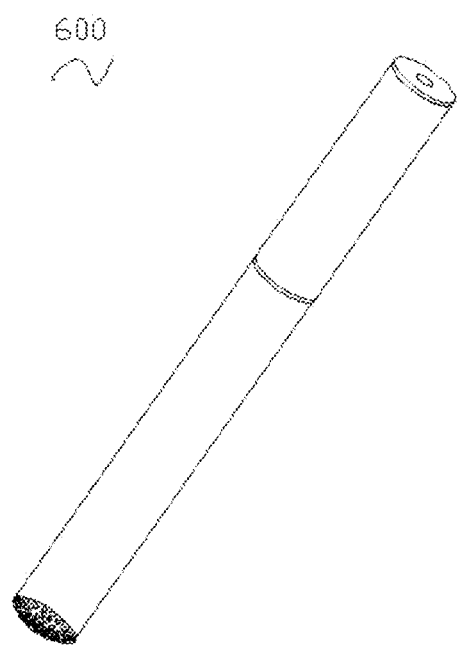
FIG. 13 is a schematic view of an electronic cigarette in accordance with a six embodiment.

Referring to FIG. 13, an electronic cigarette 600 in accordance with a six embodiment is provided. The electronic cigarette 600 includes an atomizing device and a battery assembly electrically connected to the atomizing device.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. A cartridge of an electronic cigarette, the cartridge comprising:
   an oil reserving pipe comprising an inner space for reserving a tobacco oil;
   an oil obstructing plug arranged at an end of the oil reserving pipe and comprising at least one oil hole in communication with the inner space;
   a heating assembly arranged under the oil obstructing plug and configured for heating and atomizing the tobacco oil penetrating through the at least one oil hole; and
   a sealing cover arranged at an opposite end of the oil reserving pipe, and the sealing cover comprising a curved air pressure adjusting portion facing toward the inner space of the oil reserving pipe.

2. The cartridge of claim 1, wherein the inner space is a hollow space without an oil reserving cotton.

3. The cartridge of claim 1, wherein the sealing cover comprises an oil filling hole and an air cutout formed at a peripheral wall of the sealing cover.

4. The cartridge of claim 1, wherein the oil reserving pipe comprises a peripheral wall and a bottom wall integrally formed with the peripheral wall, the peripheral wall and the bottom wall cooperatively forming the inner space.

5. The cartridge of claim 1, further comprising a heating assembly fixing base fixing and supporting the heating assembly.

6. The cartridge of claim 5, wherein the heating assembly fixing base comprises an annular projection extending upwards from a bottom surface of the heating assembly fixing base, the heating assembly arranged on the annular projection.

7. The cartridge of claim 6, wherein the heating assembly fixing base further comprises a flange extending outwards from an outer wall of the annular projection and two arms extending upwards from a top surface of the flange, annular projection being located between the arms.

8. The cartridge of claim 1, wherein a cross sectional area of the least one oil hole is in a range between 0.5-2.2 mm$^2$.

9. An atomizing device of an electronic cigarette, the atomizing device comprising:
   an atomizing sleeve;
   an electrode assembly arranged at an end of the atomizing sleeve;
   a cartridge received in the atomizing sleeve, the cartridge comprising:
      an oil reserving pipe comprising an inner space for reserving a tobacco oil;
      an oil obstructing plug arranged at an end of the oil reserving pipe and comprising an oil hole in communication with the inner space; and
      a heating assembly arranged under the oil obstructing plug and configured for heating and atomizing the tobacco oil penetrating through the oil hole;
   wherein the electrode assembly is electrically connected to the heating assembly; and
   a sealing cover arranged at an opposite end of the oil reserving pipe, the sealing cover comprising a curved air pressure adjusting portion facing toward the inner space of the oil reserving pipe.

10. The atomizing device of claim 9, wherein the sealing cover comprises an oil filling hole and an air cutout formed at a peripheral wall of the sealing cover.

11. The atomizing device of claim 10, wherein an air passage is defined between the atomizing sleeve and the oil reserving pipe, and the air cutout is in communication with the air passage.

12. The atomizing device of claim 10, further comprising a suction nozzle arranged at an opposite end of the atomizing sleeve and adjacent to the sealing cover.

13. The atomizing device of claim 9, wherein the electrode assembly comprises a screw sleeve fixed in the atomizing sleeve, an insulated ring and an electrode ring, the insulated ring being located between the screw sleeve and the electrode ring.

14. The atomizing device of claim 9, further comprising a fastening member fixed at an outer wall of the atomizing sleeve.

15. The atomizing device of claim 14, wherein the atomizing sleeve is made of a plastic material, and the fastening member is made of a metallic material.

16. An electronic cigarette comprising a battery assembly and an atomizing device of claim 8, the battery assembly configured for being electrically connected to the atomizing device.

* * * * *